United States Patent
Zhou et al.

(10) Patent No.: US 11,707,605 B2
(45) Date of Patent: Jul. 25, 2023

(54) EXPANDABLE SHEATH WITH LONGITUDINALLY EXTENDING REINFORCING MEMBERS

(71) Applicant: Edwards Lifesciences Corporation, Irvine, CA (US)

(72) Inventors: Pu Zhou, Dove Canyon, CA (US); Erik Bulman, Lake Forest, CA (US); Baigui Bian, Laguna Niguel, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 23 days.

(21) Appl. No.: 17/068,632

(22) Filed: Oct. 12, 2020

(65) Prior Publication Data

US 2021/0023344 A1 Jan. 28, 2021

Related U.S. Application Data

(63) Continuation of application No. 15/914,748, filed on Mar. 7, 2018, now Pat. No. 10,799,685.
(Continued)

(51) Int. Cl.
*A61M 25/04* (2006.01)
*A61M 25/06* (2006.01)
(Continued)

(52) U.S. Cl.
CPC ....... *A61M 25/0662* (2013.01); *A61F 2/2436* (2013.01); *A61M 25/0023* (2013.01);
(Continued)

(58) Field of Classification Search
CPC .......... A61M 25/0662; A61M 25/0023; A61M 25/005; A61M 2025/0024;
(Continued)

(56) References Cited

U.S. PATENT DOCUMENTS 4,601,713 A 7/1986 Fuqua
4,710,181 A 12/1987 Fuqua
(Continued)

FOREIGN PATENT DOCUMENTS

EP 0103546 A1 3/1984
EP 0592410 B1 10/1995
(Continued)

OTHER PUBLICATIONS

510K Premarket Notification, Jun. 22, 2018.
BSX Structural Heart Update 2018.

*Primary Examiner* — Erich G Herbermann
(74) *Attorney, Agent, or Firm* — Meunier Carlin Curfman LLC; Sean Seung Kyu Kim

(57) ABSTRACT

An expandable delivery sheath includes an elastic outer tubular layer and an inner tubular layer. The inner tubular layer include a thick wall portion integrally connected to a thin wall portion. The thin wall portion can include longitudinal reinforcing members/rods that facilitate unfolding during the passage of the implant, thus decreasing the push force and increasing the consistency of the push force. The inner tubular layer can have a non-expanded or folded condition wherein the thin wall portion folds onto an outer surface of the thick wall portion under urging of the elastic outer tubular layer. When an implant passes therethrough, the outer tubular layer stretches and the inner tubular layer unfolds into an expanded lumen diameter. Once the implant passes, the outer tubular layer again urges the inner tubular layer into the non-expanded condition with the sheath reassuming its smaller profile.

19 Claims, 14 Drawing Sheets

Related U.S. Application Data

(60) Provisional application No. 62/469,121, filed on Mar. 9, 2017.

(51) Int. Cl.
*A61M 25/00* (2006.01)
*A61F 2/24* (2006.01)
*A61F 2/958* (2013.01)

(52) U.S. Cl.
CPC .............. *A61F 2/2433* (2013.01); *A61F 2/958* (2013.01); *A61M 25/005* (2013.01); *A61M 2025/0024* (2013.01)

(58) Field of Classification Search
CPC .......... A61M 2560/0406; A61F 2/2436; A61F 2/2433; A61F 2/958
See application file for complete search history.

(56) References Cited

U.S. PATENT DOCUMENTS

| | | | |
|---|---|---|---|
| 4,738,666 A | 4/1988 | Fuqua |
| 4,921,479 A | 5/1990 | Grayzel |
| 5,104,388 A | 4/1992 | Quackenbush |
| 5,318,588 A | 6/1994 | Horzewski et al. |
| 5,320,611 A | 6/1994 | Bonutti et al. |
| 5,484,418 A | 1/1996 | Quiachon et al. |
| 5,501,667 A | 3/1996 | Verduin, Jr. |
| 5,674,240 A | 10/1997 | Bonutti et al. |
| 5,810,776 A | 9/1998 | Bacich et al. |
| 5,817,100 A | 10/1998 | Igaki |
| 5,997,508 A | 12/1999 | Lunn et al. |
| 6,080,141 A | 6/2000 | Castro et al. |
| 6,090,072 A | 7/2000 | Kratoska et al. |
| 6,090,136 A | 7/2000 | McDonald et al. |
| 6,190,357 B1 | 2/2001 | Ferrari et al. |
| 6,312,443 B1 | 11/2001 | Stone |
| 6,346,092 B1 | 2/2002 | Leschinsky |
| 6,358,238 B1 | 3/2002 | Sherry |
| 6,443,979 B1 | 9/2002 | Stalker et al. |
| 6,494,860 B2 | 12/2002 | Rocamora et al. |
| 6,632,236 B2 | 10/2003 | Hogendijk |
| 6,652,492 B1 | 11/2003 | Bell et al. |
| 6,814,715 B2 | 11/2004 | Bonutti et al. |
| 6,899,727 B2 | 5/2005 | Armstrong et al. |
| 7,438,712 B2 | 10/2008 | Chouinard |
| 7,591,832 B2 | 9/2009 | Eversull et al. |
| 7,655,016 B2 | 2/2010 | Demarais et al. |
| 7,665,016 B2 | 2/2010 | Behrens et al. |
| 7,678,128 B2 | 3/2010 | Boyle et al. |
| 7,713,193 B2 * | 5/2010 | Nance .............. A61B 17/3439 600/184 |
| 7,762,995 B2 | 7/2010 | Eversull et al. |
| 7,766,820 B2 | 8/2010 | Core |
| 7,780,692 B2 | 8/2010 | Nance et al. |
| 7,785,360 B2 | 8/2010 | Freitag |
| 7,837,692 B2 | 11/2010 | Mulholland et al. |
| 7,892,203 B2 | 2/2011 | Lenker et al. |
| 7,927,309 B2 | 4/2011 | Palm |
| 7,963,952 B2 | 6/2011 | Wright, Jr. et al. |
| 8,034,072 B2 | 10/2011 | Nguyen et al. |
| 8,048,034 B2 | 11/2011 | Eversull et al. |
| 8,090,936 B2 | 1/2012 | Fallon et al. |
| 8,092,481 B2 | 1/2012 | Nance et al. |
| 8,252,015 B2 | 8/2012 | Leeflang et al. |
| 8,282,664 B2 | 10/2012 | Nance et al. |
| 8,414,645 B2 | 4/2013 | Dwork et al. |
| 8,562,559 B2 | 10/2013 | Bishop et al. |
| 8,562,673 B2 | 10/2013 | Yeung et al. |
| 8,652,203 B2 | 2/2014 | Quadri et al. |
| 8,668,668 B2 | 3/2014 | Bishop et al. |
| 8,790,387 B2 | 7/2014 | Nguyen et al. |
| 9,044,577 B2 | 6/2015 | Bishop et al. |
| 9,192,751 B2 | 11/2015 | Macaulay et al. |
| 9,192,752 B2 | 11/2015 | Leeflang et al. |
| 9,254,374 B2 | 2/2016 | Thorstenson et al. |
| 9,259,813 B2 | 2/2016 | Heideman et al. |
| 9,301,840 B2 | 4/2016 | Nguyen et al. |
| 9,301,841 B2 | 4/2016 | Nguyen et al. |
| 9,320,508 B2 | 4/2016 | Carroux |
| 9,393,041 B2 | 7/2016 | Barker et al. |
| 9,642,704 B2 | 5/2017 | Tuval et al. |
| 9,788,944 B2 | 10/2017 | Daly et al. |
| 9,907,931 B2 | 3/2018 | Birmingham et al. |
| 2002/0032459 A1 | 3/2002 | Horzewski et al. |
| 2002/0123793 A1 | 9/2002 | Schaldach et al. |
| 2003/0004537 A1 | 1/2003 | Boyle et al. |
| 2004/0087968 A1 | 5/2004 | Core |
| 2004/0122415 A1 | 6/2004 | Johnson |
| 2005/0080430 A1 | 4/2005 | Wright et al. |
| 2005/0085842 A1 | 4/2005 | Eversull et al. |
| 2005/0125021 A1 | 6/2005 | Nance et al. |
| 2006/0020321 A1 | 1/2006 | Parker |
| 2006/0052750 A1 * | 3/2006 | Lenker ................ A61M 27/008 604/164.01 |
| 2006/0135962 A1 | 6/2006 | Kick et al. |
| 2006/0135981 A1 | 6/2006 | Lenker et al. |
| 2006/0217755 A1 | 9/2006 | Eversull et al. |
| 2007/0021768 A1 | 1/2007 | Nance et al. |
| 2007/0074805 A1 | 4/2007 | Leeflang et al. |
| 2007/0087148 A1 | 4/2007 | Okushi et al. |
| 2008/0004521 A1 | 1/2008 | Hundley et al. |
| 2008/0004571 A1 | 1/2008 | Voss |
| 2008/0114331 A1 | 5/2008 | Holman et al. |
| 2008/0243081 A1 | 10/2008 | Nance et al. |
| 2010/0094209 A1 | 4/2010 | Drasler et al. |
| 2010/0094392 A1 | 4/2010 | Nguyen et al. |
| 2010/0198160 A1 | 8/2010 | Voss |
| 2011/0112567 A1 | 5/2011 | Lenker et al. |
| 2011/0190697 A1 | 8/2011 | Farnan |
| 2011/0251681 A1 | 10/2011 | Shipley et al. |
| 2012/0083877 A1 * | 4/2012 | Nguyen ................ A61F 2/2418 623/2.11 |
| 2012/0116439 A1 | 5/2012 | Ho |
| 2012/0158033 A1 | 6/2012 | Deal et al. |
| 2012/0323180 A1 | 12/2012 | Chebator et al. |
| 2013/0131718 A1 | 5/2013 | Jenson et al. |
| 2013/0178711 A1 | 7/2013 | Avneri et al. |
| 2013/0231735 A1 | 9/2013 | Deem et al. |
| 2013/0281787 A1 | 10/2013 | Avneri et al. |
| 2014/0121629 A1 | 5/2014 | Macaulay et al. |
| 2014/0236122 A1 | 8/2014 | Anderson et al. |
| 2014/0236123 A1 * | 8/2014 | Birmingham ..... A61M 25/0012 604/524 |
| 2014/0379067 A1 | 12/2014 | Nguyen et al. |
| 2015/0182723 A1 | 7/2015 | Leeflang et al. |
| 2015/0238178 A1 | 8/2015 | Carroux |
| 2015/0265798 A1 | 9/2015 | Nihonmatsu et al. |
| 2015/0320971 A1 | 11/2015 | Leeflang et al. |
| 2016/0074067 A1 | 3/2016 | Furnish et al. |
| 2016/0135840 A1 | 5/2016 | Kick et al. |
| 2016/0213882 A1 * | 7/2016 | Fitterer ................ A61M 29/02 |
| 2016/0296332 A1 | 10/2016 | Zhou et al. |
| 2016/0296730 A1 | 10/2016 | Zhou et al. |
| 2017/0014157 A1 | 1/2017 | Coyle et al. |
| 2017/0072163 A1 | 3/2017 | Lim et al. |
| 2017/0209133 A1 | 7/2017 | Ciulla et al. |
| 2017/0245864 A1 | 8/2017 | Franano et al. |
| 2017/0252062 A1 | 9/2017 | Fitterer et al. |
| 2018/0161064 A1 | 6/2018 | Fitterer et al. |
| 2018/0199960 A1 | 7/2018 | Anderson et al. |
| 2018/0229000 A1 | 8/2018 | Anderson et al. |

FOREIGN PATENT DOCUMENTS

| | | | |
|---|---|---|---|
| EP | 1139889 A1 | 10/2001 |
| EP | 1694398 A2 | 8/2006 |
| EP | 1793881 A2 | 6/2007 |
| EP | 1804860 A2 | 7/2007 |
| EP | 2101661 A1 | 9/2009 |
| EP | 2288403 A2 | 3/2011 |
| EP | 2475417 A2 | 7/2012 |
| EP | 2862590 A1 | 4/2015 |
| EP | 2911729 A1 | 9/2015 |

(56) References Cited

FOREIGN PATENT DOCUMENTS

| | | |
|---|---|---|
| EP | 2995268 A1 | 3/2016 |
| JP | 2012040145 A | 3/2012 |
| WO | 2004037333 A1 | 5/2004 |
| WO | 2008147964 A1 | 12/2008 |
| WO | 2009035745 A1 | 3/2009 |
| WO | 2013044942 A1 | 4/2013 |
| WO | 2014140093 A1 | 9/2014 |
| WO | 2018148488 A1 | 8/2018 |

* cited by examiner

EXPANDABLE SHEATH WITH LONGITUDINALLY EXTENDING REINFORCING MEMBERS

CROSS-REFERENCE TO RELATED APPLICATIONS

This application is a continuation of application Ser. No. 15/914,748, filed on Mar. 7, 2018, (now U.S. Pat. No. 10,799,685), which claims the benefit of priority to U.S. Provisional Application No. 62/469,121, filed Mar. 9, 2017, which are incorporated by reference in their entirety for all purposes.

FIELD

The present application is directed to a sheath for use with catheter-based technologies for repairing and/or replacing heart valves, as well as for delivering an implant, such as a prosthetic valve to a heart via the patient's vasculature.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

U.S. Pat. No. 8,790,387, which is entitled "Expandable Sheath for Introducing an Endovascular Delivery Device into a Body" and is incorporated herein by reference, discloses a sheath with a split outer polymeric tubular layer and an inner polymeric layer. A portion of the inner polymeric layer extends through a gap created by the cut and can be compressed between the portions of the outer polymeric tubular layer. Upon expansion of the sheath, portions of the outer polymeric tubular layer have separated from one another, and the inner polymeric layer is expanded to a substantially cylindrical tube. Advantageously, the sheath disclosed in the '387 patent can temporarily expand for passage of implantable devices and then return to its starting diameter.

U.S. patent application Ser. No. 14/880,109, titled "Expandable Sheath" and described in U.S. Patent Application Publication No. 2016/0296730, incorporated herein by reference, discloses an inner tubular member having a longitudinally extending thin wall portion that is folded between surrounding thick wall portions when the inner tubular member is in the non-expanded state. This thin segment facilitates the expansion and collapse of the inner tubular layer while also maintaining a fluid seal to prevent leakage during use.

Despite the disclosures of the '387 patent and the '109 application, there remains a need for further improvements in introducer sheaths for endovascular systems used for implanting valves and other prosthetic devices. Even further reduction of the profile is desirable to provide the most protection for the vascular wall. However, reduction of the profile tends to increase the necessary push force (the force required to push a device through the sheath). It is helpful if the consistency of the push force is maintained as the device travels the length of the sheath, but this can be difficult to achieve. For example, the process of unfolding the inner tubular layer of the sheath described in application '109 can create inconsistency in the necessary push force. These inconsistencies can result in a practitioner using more force than is needed to pass a difficult spot, possibly causing unnecessary damage to the vascular wall.

SUMMARY

Disclosed herein are low-profile expandable introducer sheaths and methods of using the same to achieve low and consistent push force during intravascular procedures. The sheaths are adapted to temporarily expand a portion of the sheath to allow for the passage of a delivery system for a cardiovascular device, then return to a non-expanded state after the passage of the system. The sheath includes an elastic outer tubular layer and an inner tubular layer through which the cardiovascular device and its delivery system pass. The inner tubular layer includes a thick wall portion integrally connected to a thin wall portion. The thick wall portion having a first and second longitudinally extending end, the thin wall portion extending therebetween. The thin wall portion includes at least one longitudinal rod/reinforcing member extending along a length of the thin wall portion. When the implant passes therethrough, the outer tubular layer stretches and the inner tubular layer at least partially unfolds to a larger expanded diameter to accommodate the diameter of the implant. Once the implant passes, the outer tubular layer again urges the inner tubular layer into the folded configuration with the sheath reassuming its smaller profile. The sheath can also include selectively placed longitudinal rods that mediate friction between the inner and outer tubular layers, or between folds of the inner tubular layer to facilitate easy expansion and collapse. This reduces the overall push force and increases the consistency of the push force needed the advance the oversized implant through the sheath's lumen. The lower and more consistent push force facilitates a reduction in the profile size. Furthermore, the integral construction of the inner tubular layer guards against the leaks and snags of prior art split-tube and uniform thickness liner combinations.

Embodiments include an expandable sheath including an elastic outer tubular layer and an inner tubular layer. The inner tubular layer has a thick wall portion integrally connected to a thin wall portion—such as by co-extrusion during manufacture. The thick wall portion having a first and second longitudinally extending end, the thin wall portion extending therebetween. The thin wall portion can include a longitudinal rod/reinforcing member extending along a length of the thin wall portion. The elastic outer tubular layer and the inner tubular layer can be radially movable between an expanded state and a non-expanded state. In the non-expanded state the elastic outer tubular layer can urge the first longitudinally extending end towards and/or under the second longitudinally extending end of the inner tubular layer. In the expanded state, the first and second longitudinally extending ends of the inner tubular layer expand apart with the thin wall portion extending therebetween. The outer elastic tubular layer can urge the inner tubular layer towards the non-expanded state. The outer diameter of the elastic outer tubular layer can be from 10 French to 14 French in the non-expanded state. In an example sheath, the distal portion of the outer tubular layer and a distal portion of the inner tubular layer are adhered to each other in a sealed configuration.

The longitudinal rods can extend within in the thin wall portion of the inner tubular layer such that the rod has a thickness no greater than a thickness of the thin wall portion. A surface of the rod can protrude from a surface of the inner tubular layer. In an example sheath, the surface of the rod can protrude from an inner surface of the inner tubular layer such that the surface of the rod facilitates relative movement between the inner tubular layer and a passing device. In another example sheath, the surface of the rod can protrude from an outer surface of the inner tubular layer such that the surface of the rod facilitates relative movement between the inner tubular layer and the outer tubular layer. In another example sheath, a first portion of an outer surface of the rod can protrude from an inner surface of the inner tubular member and a second portion of the outer surface of the rod can protrude from an outer surface of the inner tubular layer. The longitudinal rod can extend along the entire length of the inner tubular layer. The longitudinal rod can have a curvilinear, rectilinear, and irregular shape in cross-section. In one example embodiment, the rod has a circular shape in cross-section.

In another embodiment, the longitudinal rods can also be included on the thick wall portion of the inner tubular layer. In an example sheath, the outer tubular layer can include a plurality of longitudinal rods, a portion of each of the plurality of longitudinal rods extending into a central lumen defined by the outer tubular layer such that the plurality of longitudinal rods provide a bearing surface to facilitate relative movement of the inner tubular layer within the outer tubular layer when moving between the expanded and non-expanded state. In another example sheath, a distal portion of the outer tubular layer and a distal portion of the inner tubular layer are adhered to each other in a sealed configuration.

A method of delivering a device into the blood vessel of a patient using the expandable introducer sheath can include inserting an expandable sheath at an implantation site within the blood vessel of the patient and advancing the device through a lumen of the expandable sheath. The sheath can include a thick wall portion and a thin wall portion extending between longitudinally extending ends of the thick wall portion, the thin wall portion including a longitudinally extending reinforcing member extending along a length of the thin wall portion. The method can further include locally expanding a portion of the sheath from a non-expanded state to an expanded state by a radially outward force provided at an inner surface of the sheath by advancement of the device, such that expansion of the sheath causes the longitudinally extending ends of the inner tubular layer to expand apart with the thin wall portion extending therebetween. Upon passage of the device from the portion of the sheath, the portion of the sheath can be locally contracted from the expanded state at least partially back to a non-expanded state. In the non-expanded state, the longitudinally extending ends of the thick wall portion can overlap such that the thin wall portion extends between the overlapping portions of the thick wall portion. In the expanded state, the longitudinally extending ends can expand apart with the thin wall portion extending therebetween.

In an example sheath, the longitudinally extending ends of the thick wall portion can include a first longitudinally extending end and a second longitudinally extending end. Locally expanding a portion of the sheath can further include incrementally expanding the sheath, the first increment of expansion provided between the first longitudinally extending end and the reinforcing member, the second increment of expansion provided between the reinforcing member and the second longitudinally extending end.

In another example sheath, the longitudinally extending ends of the thick wall portion can include a first longitudinally extending end and a second longitudinally extending end. The thin wall portion of the expandable sheath can further include a first and a second longitudinally extending reinforcing member. Locally expanding a portion of the sheath can further comprise incrementally expanding the sheath, the first increment of expansion provided between the first longitudinally extending end and the first reinforcing member, the second increment of expansion provided between first reinforcing member and the second reinforcing member, the third increment of expansion provided between the second reinforcing member and the second longitudinally extending end.

Locally contracting the sheath can comprise providing inwardly directed radial force of an elastic outer layer that exerts a radially compressive force urging the sheath towards the non-expanded state.

In an example sheath, the longitudinally extending ends of the thick wall portion include a first longitudinally extending end and a second longitudinally extending end. Locally contracting the sheath further comprises moving the first and second longitudinally extending ends towards each other and into an overlapping configuration.

DETAILED DESCRIPTION

Figure 1A:
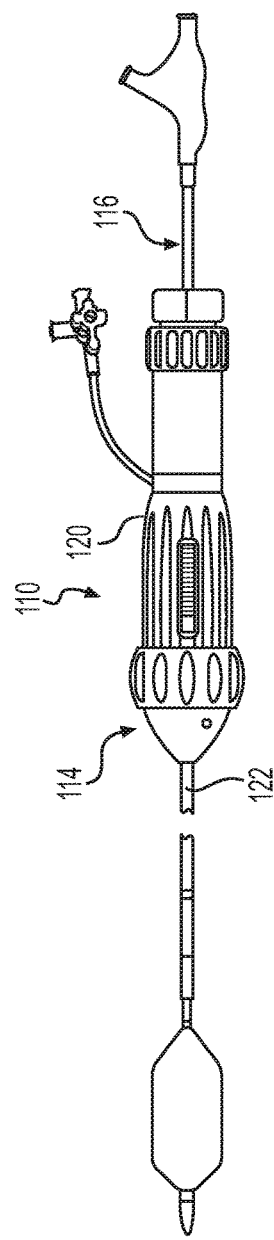
FIGS. 1A-1C show a delivery catheter assembly for delivering a prosthetic implant.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of a sheath, catheter, or delivery assembly. "Proximal" means that region closest to handle of the device, while "distal" means that region farthest away from the handle of the device.

Disclosed herein are elongate, expandable introducer sheaths that are particularly suitable for use in the delivery of implants in the form of implantable heart valves, such as balloon-expandable implantable heart valves. Balloon-expandable implantable heart valves are well-known and will not be described in detail here. An example of such an implantable heart valve is described in U.S. Pat. No. 5,411,552, and also in U.S. Patent Application Publication No. 2012/0123529, both of which are hereby incorporated by reference. The elongate expandable introducer sheaths disclosed herein can also be used with the delivery systems for other types of implantable devices, such as self-expanding implantable heart valves, stents or filters. The term "implantable" as used herein is broadly defined to mean anything—prosthetic or not—that is delivered to a site within a body. A diagnostic device, for example, can be an implantable.

Disclosed embodiments of an expandable introducer sheath can minimize trauma to the vessel by allowing for temporary expansion of a portion of the introducer sheath to accommodate the implantable device and its delivery system, then return fully or partially to the original, non-expanded diameter after passage of the device. The expandable sheath can include an integrally formed inner tubular layer with thick and thin wall portions. The thin wall portion can expand to provide an expanded central lumen to allow passage of an implant. The inner layer folds back onto itself under biasing of an outer elastic tubular layer following passage of the implant.

In another aspect, the expandable sheath can include one or more longitudinally oriented stiffening elements, such as rods. When coupled to the thin wall portion of the inner tubular layer, the longitudinal rods facilitate unfolding during expansion, decreasing the required push force to move the device through the sheath while also increasing the consistency of the push force. The push force is decreased because the longitudinal rods lower the friction between the surfaces of the thin and thick wall segments when the inner tubular member is in a folded state, making it easier for them to slide against each other during unfolding. The longitudinal rods also improve the consistency of the push force by causing unfolding to occur at specific points along the thin wall segment.

Some embodiments can comprise an expandable introducer sheath with a smaller profile than the profiles of prior art introducer sheaths. The smaller profiles are made possible, at least in part, by the lower and more consistent push force. Finally, present embodiments can reduce the length of time a procedure takes, as well as reduce the risk of a longitudinal or radial vessel tear, or plaque dislodgement, because only one introducer sheath is required, rather than several different sheaths of gradually increasing diameters. Embodiments of the present expandable sheath can avoid the need for multiple insertions for the dilation of the vessel.

Figure 1B:
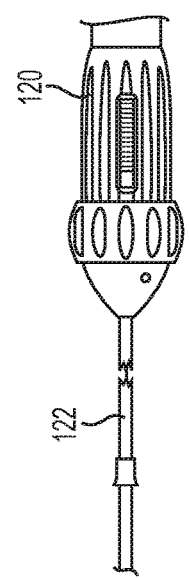
Figure 1C:
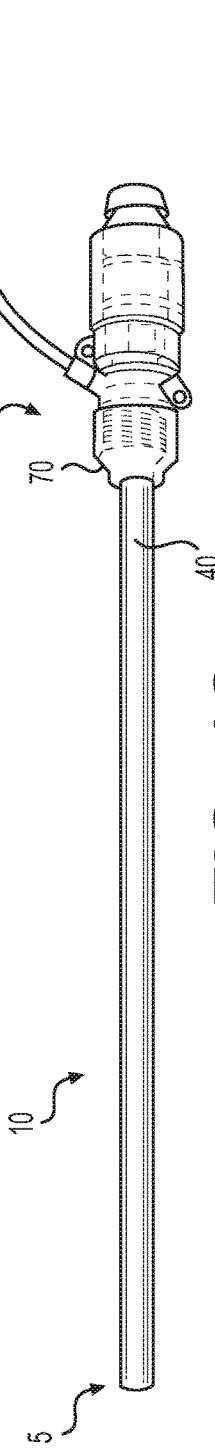

FIGS. 1A-1C illustrate a sheath 10 according to the present disclosure in use with a representative delivery apparatus 110 for delivering a prosthetic implant 112, such as a prosthetic heart valve, to a patient. It should be understood that the delivery apparatus 110 described herein is exemplary only, and that other similar delivery systems can of course be used with the expandable sheath 10. The delivery apparatus 110 generally includes a steerable guide catheter 114 and a balloon catheter 116 extending through the guide catheter 114.

The guide catheter 114 and the balloon catheter 116 illustrated in FIGS. 1A-1C are adapted to slide longitudinally relative to each other to facilitate delivery and positioning of prosthetic heart valve 112 at an implantation site in a patient's body, as described in detail below. The guide catheter 114 includes a handle portion 120 coupled to an elongated guide tube/shaft 122 (FIG. 1B).

FIG. 1C provides a perspective view of an expandable sheath 10 that is used to introduce the delivery apparatus 110 into the patient's body. The expandable sheath 10 has a central lumen to guide passage of the delivery system for the prosthetic heart valve 112. At a proximal end the expandable sheath 10 includes a hemostasis valve that prevents leakage of pressurized blood. Generally, during use a distal end of the sheath 10 is passed through the skin of the patient and inserted into a vessel, such as the femoral artery. The delivery apparatus 110 is then inserted into the sheath 10 through the hemostasis valve, and advanced through the patient's vasculature where the implant 112 is delivered and implanted within the patient.

As outlined above, the sheath 10 includes an inner tubular layer 42 and outer tubular layer 40. In FIG. 1C only the outer tubular layer 40 is visible. The sheath 10 comprises a proximal end 3 and distal end 5 opposite the proximal end 3. The sheath 10 can include a taper tube 70, a flared proximal end. The taper tube 70 can be coextruded with the sheath 10 or added to the proximal end 3 by flaring and bonding the inner and outer tubular layers 42, 40. The distal end 5 of the sheath 10 can define a tubular structure with a slightly tapering or frusto-conical distal end. The structure of the distal tip of the sheath 10 helps to increase the structural rigidity of the distal end of the tubular wall structure, blocks blood flow between the layers and provides a smooth, tapered profile for pushing through tissue when advanced over a wire or dilator.

Figure 2:
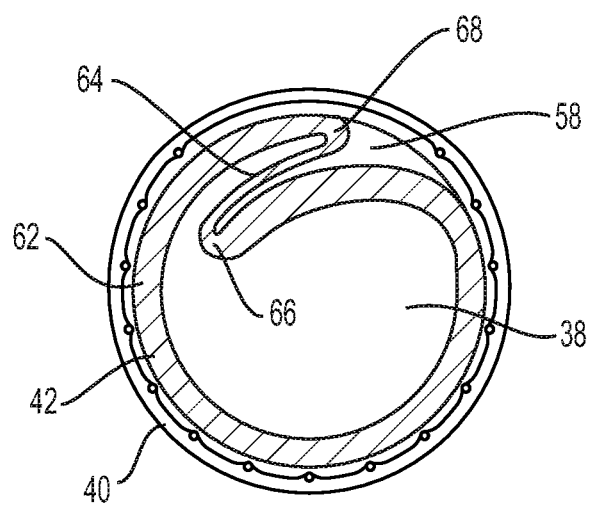
FIG. 2 is a cross-section of both the inner and outer tubular layers of the sheath in a non-expanded state.
Figure 3:
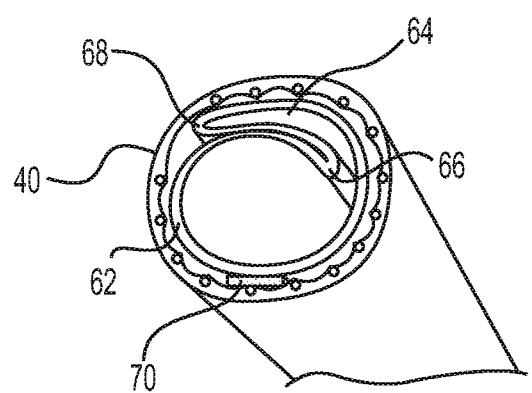
FIG. 3 is a perspective view of the distal end of an example expandable sheath.

FIGS. 2 and 3 provide various cross-sectional views of an example expandable sheath 10. The sheath 10 has a tubular wall structure including an elastic outer tubular layer 40 and an inner tubular layer 42. FIGS. 2 and 3 illustrate the inner tubular layer 42 and elastic outer tubular layer 40 in a non-expanded state. In the non-expanded state, a portion of the inner tubular layer 42 is folded over upon itself to fit within the central lumen 58 of the outer tubular layer 40. In some embodiments, the inner and outer tubular layers 42, 40 can be adhered to each other at the distal end of the sheath 10 in a sealed configuration.

Figure 4:
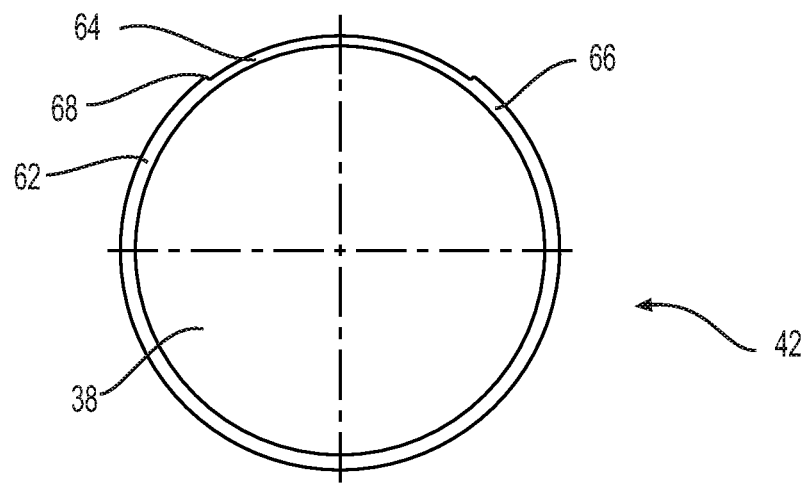
FIG. 4 is a cross-section of an example inner tubular layer of the sheath.

FIG. 4 provides a cross-sectional view of an example inner tubular layer 42 in an expanded state. As illustrated in FIG. 4, the inner tubular layer 42 can include a thick wall portion 62 integrally connected with a thin wall portion 64. The thick wall portion 62 is approximately 0.011+/−0.003 inches and the thin wall portion 64 is approximately 0.0055+/−0.0020 inches. The inner tubular layer 42 is preferably constructed of a relatively (compared to the outer tubular layer 40) stiff material such as a stiff polymer like high density polyethylene (HDPE) or an equivalent polymer.

The thick wall portion 62, in the illustrated embodiment of FIG. 4, has a C-shaped cross-section with a first longitudinally extending end 66 and a second longitudinally extending end 68. At the ends 66, 68, the thickness of the thick wall portion 62 starts to narrow to thin wall portion 64 on the cross-section. That transition extends longitudinally in the direction of the axis of the sheath 10, such that the thick wall portion 62 forms an elongate C-shaped member.

The thin wall portion 64 extends between the longitudinally extending ends 66, 68 of the thick wall portion 62 to define the tubular shape of the inner tubular layer 42. As illustrated in FIGS. 2 and 3, in the non-expanded state, the elastic outer tubular layer 40 urges the first longitudinally extending end 66 toward and/or under the second longitudinally extending end 68 of the inner tubular layer 42. This causes the thin wall portion 64 to fold and be positioned between the first and second longitudinally extending ends 66, 68 of the thick wall portion 62.

In an example sheath 10, the central lumen 38 of the inner tubular layer 42, in the expanded state, has a diameter larger than the initial, non-expanded, diameter of the central lumen 58 of the elastic outer tubular layer 40. For example, the expanded diameter of the central lumen 38 of the inner tubular layer 42 is about 0.300+/−0.005 inches. The initial, non-expanded, diameter of the central lumen 58 of the outer tubular layer 40 is about 0.185 inches. In another example, the expanded diameter of the central lumen 38 of the inner tubular layer is about 0.255+/−0.005 inches and the initial, non-expanded, diameter of the central lumen 58 of the outer tubular layer 40 is about 0.165 inches +/−0.005. The elastic outer tubular layer 40 can expand to accommodate this increase in diameter of the inner tubular layer 42.

Figure 5:
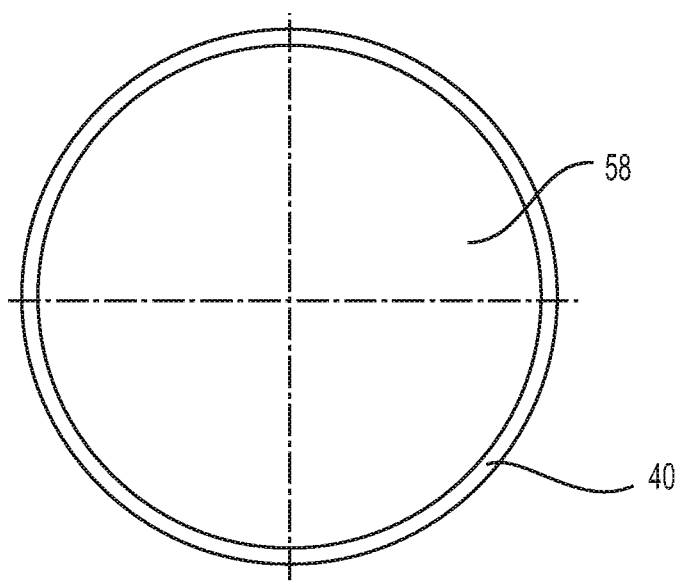
FIG. 5 is a cross-section of an example outer tubular layer of the sheath.

FIG. 5 provides a cross-sectional view of an example outer tubular layer 40. As illustrated, the outer tubular layer 40 has a cylindrical shape with a circular cross-section along its entire length. The outer tubular layer 40 defines a central lumen 58 extending axially through its cylindrical cross-section. The diameter of the outer tubular layer 40 in its fully expanded state is sized so as to accommodate the implant and its delivery apparatus 110. In one example sheath, upon expansion, the diameter of the central lumen 58 of the outer tubular layer 40 can be 0.322 inches, the outer tubular layer itself having a wall thickness of 0.005+/−0.003 inches to accommodate delivery of a stent-mounted heart valve. In one aspect, inner surface of the outer tubular layer 40 and/or outer surface of the inner tubular layer 42 can be treated to have or have applied thereto a lubricious coating to facilitate unfolding and folding of the inner tubular layer 42.

The central lumen 58 of the outer tubular layer 40 is referred to as having "initial" diameter to designate its passive, non-expanded, or as-formed diameter or cross-sectional dimension when not under the influence of outside forces, such as the implant 112 and its delivery system passing therethrough. In an example sheath 10, the outer tubular layer 40 can be constructed from an elastic material and may not retain its shape under even light forces such as gravity. Also, the outer tubular layer 40 need not have a cylindrical cross-section and instead could have oval, square or any other regular or irregular shape in cross-section which generally can be configured to meet the requirements of the inner tubular layer 42 and/or expected shape of the implant 112. Thus, the term "tube" or "tubular" as used herein is not meant to limit shapes to circular cross-sections. Instead, tube or tubular can refer to any elongate structure with a closed-cross section and lumen extending axially therethrough.

The outer tubular layer 40, in one implementation, is constructed of a relatively elastic material having sufficient flexibility to accommodate the expansion induced by passage of the implant and its delivery system and expansion of the inner tubular layer 42 while, at the same time, having enough material stiffness to urge the inner tubular layer 42 back into/towards a non-expanded state having an approximation of the initial diameter once the implant has passed. An exemplary material includes NEUSOFT. NEUSOFT is a translucent polyether urethane based material with good elasticity, vibration dampening, abrasion and tear resistance. The polyurethanes are chemically resistant to hydrolysis and suitable for overmolding on polyolefins, ABS, PC, Pebax and nylon. The polyuerthane provides a good moisture and oxygen barrier as well as UV stability. One advantage of the outer tubular layer 40 is that it provides a fluid barrier for the pressurized blood. Other materials having similar properties of elasticity can also be used for the elastic outer tubular layer 40.

Figure 6A:
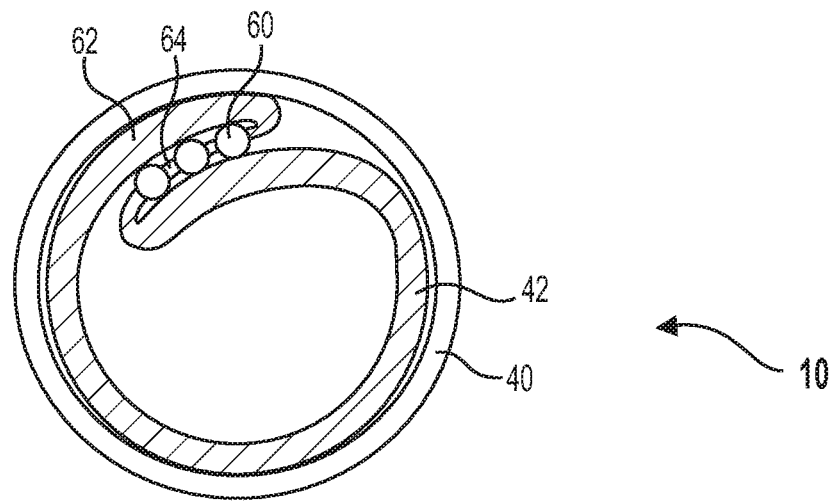
FIGS. 6A-6C are cross-sections of an example sheath including longitudinal rods in the inner tubular layer.
Figure 6B:
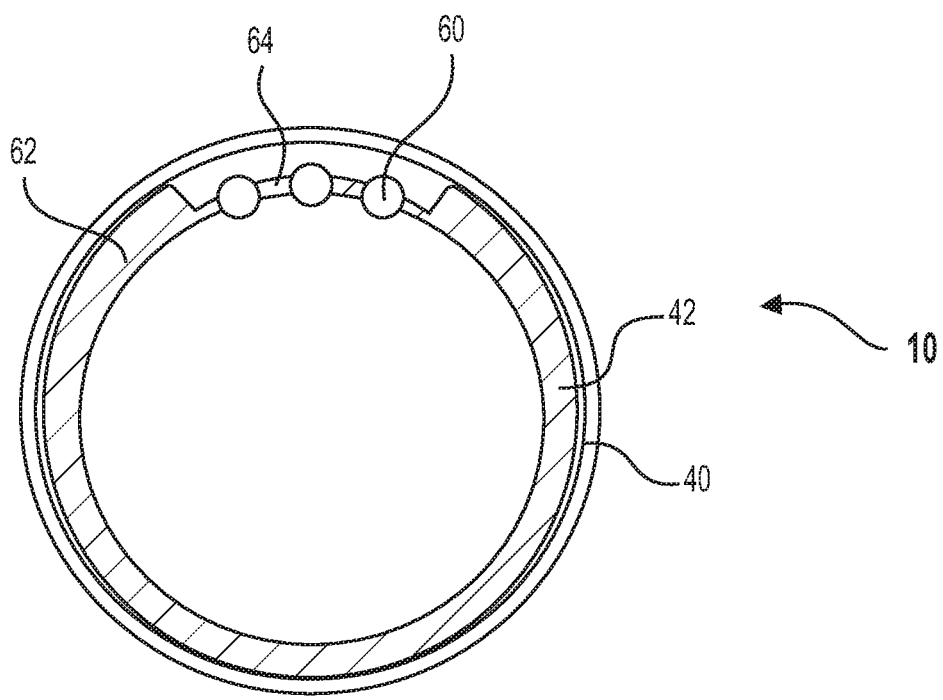
Figure 6C:
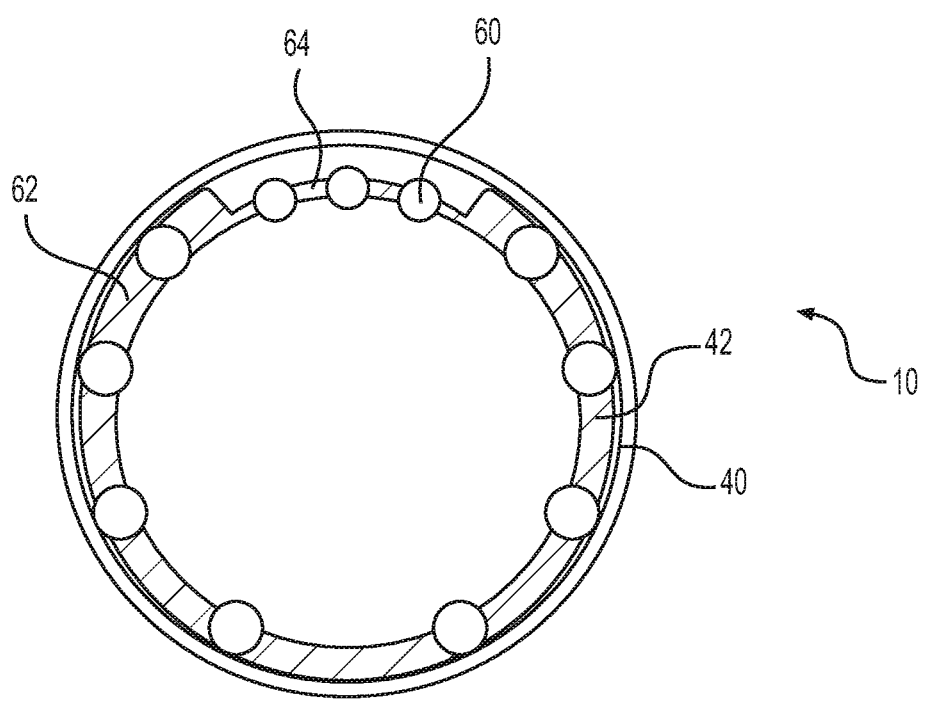

FIGS. 6A-6C illustrate a cross-sectional view of an example sheath 10 including one or more longitudinally oriented stiffening elements, such as rods 60. Advantageously, the longitudinal rods 60 are configured to provide a bearing surface to facilitate relative movement of the delivery apparatus 110 and/or prosthetic implant 112 within the inner tubular layer 42. This is especially helpful when the inner tubular layer 42 is unfolding and returning (fully or partially) to its originally folded shape upon passage of the delivery apparatus 110/prosthetic implant 112.

A sheath 10 with rods 60 coupled only to the thin wall portion 64 is shown in cross-section in the non-expanded state in FIG. 6A and the expanded state in FIG. 6B. When coupled to the thin wall portion 64 of the inner tubular layer 42, the longitudinal rods 60 reduce friction between the thin wall portion 64 and the adjacent thick wall section 62, making it easier for them to slide against each other. This reduction in friction facilitates unfolding during expansion of the sheath 10, decreasing the required push force to move the prosthetic implant and its delivery system through the sheath 10. The consistency and uniformity of the push force is also increased by the because the process of unfolding occurs at specific, incremental points along the thin wall segment. For example, during local expansion of the sheath 10, the inner tubular layer 42 can incrementally expand or have a gradual/segmented expansion such that the unfolding of the thin wall portion 64 progresses gradually between ends 66, 68 and rods 60. In one example, the incremental expansion progresses from the first end 66 to the next adjacent rod 60, to the next adjacent rod 60, and so forth between the rods 60, to the second end 68, until the inner tubular member 42 is in the expanded state and the thin wall portion 64 is no longer folded.

FIG. 6C shows longitudinal rods 60 embedded within and spaced around both the thick wall portion 62 and the thin wall portion 64, with the embedded rods 60 protruding from both the inner and outer surfaces of the inner tubular layer 42. Longitudinal rods 60 can be embedded within just the thin wall portion 64, as shown in FIGS. 6A and 6B, or the longitudinal rods 60 can be embedded within and spaced around both the thick wall portion 62 and the thin wall portion 64, as shown in FIG. 6C. The length or width of a longitudinal rod 60 positioned in the thin wall portion 64 of inner tubular layer 42 can be the same size as longitudinal rods 60 positioned in the thick wall portion 62, or a different size.

The longitudinal rods 60 can have a circular cross-section so as to present a curved bearing surface into central lumen 38 of the inner tubular layer 42 and/or central lumen 58 of the outer tubular layer 40. In this manner, the longitudinal rods 60 space the inner tubular layer 42 from the inner surface of the outer tubular layer 40 and/or the outer surface of the delivery apparatus 110/implant 112, thus reducing friction or the tendency to stick and impede relative movement. Although diameters for the longitudinal rods 60 can vary, in one embodiment they are 0.005+/−0.004 inches in diameter. In some examples, the longitudinal rod 60 extends from the inner and/or outer surface of the inner tubular layer 42 about 0.004+/−0.003 inches. In other embodiments, the longitudinal rods 60 can define other shapes in cross-section. It is also contemplated that the cross-sectional shape of the longitudinal rod 60 can change along the sheath 10 in the longitudinal direction. Alternatively, the longitudinal rods 60 can be completely encapsulated within the thin wall portion 64 of the inner tubular layer 42; that is, the outer diameter of the rods 60 can be equal to or less than the thickness of the thin wall portion 64. In this manner, the rods 60 provide the described reinforcing structure and facilitate incremental unfolding/expansion of the inner tubular layer 42, while providing relatively minimal friction reducing capabilities. The longitudinal rods 60 can be composed of the same or different material as the inner tubular layer 42. The longitudinal rods 60 can be coupled to the inner tubular layer 42 by co-extrusion, and/or embedded or otherwise coupled to the elastic material of the inner tubular layer 42.

Figure 16:
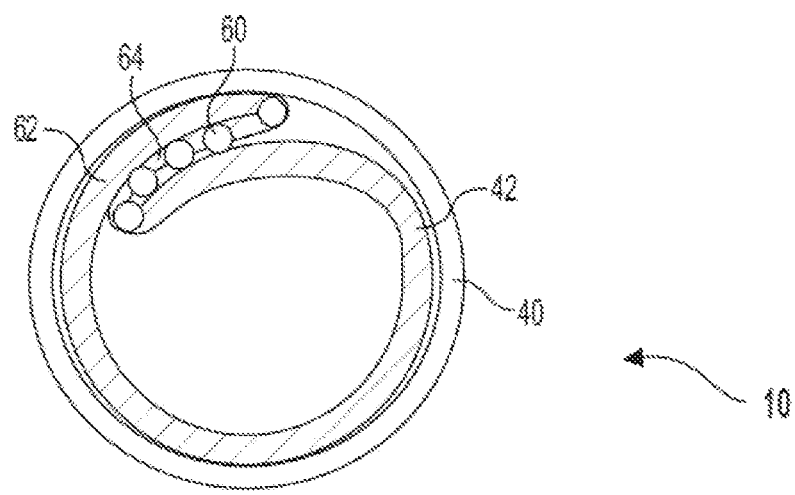
FIG. 16 is a cross-section of an example sheath including longitudinal rods in the inner tubular layer.

When the sheath 10 is in the unexpanded configuration, as in FIG. 6A, the longitudinal rods 60 contact the thick wall portion 62 on both the inner and outer surfaces of the inner tubular layer 42, spacing the thick wall portion 62 from the thin wall portion 64. The decreased contact area between the thick and thin wall portions 62, 64 diminishes the friction between the surfaces during sheath expansion. The decreased friction translates to a lower push force, i.e., less force is required to move the implant and its delivery system through the sheath 10 and towards the procedure site. Coupling longitudinal rods 60 to the thin wall portion 64 can also increase the consistency and uniformity of the push force as the implant and its delivery apparatus 110 travel along the length of sheath 10. Without the longitudinal rods 60, the thick and thin wall portions 62, 64 can separate from each other at random intervals along the thin wall portion 64 during unfolding. When the longitudinal rods 60 are present, the folding points predictably occur at expected locations. For example, if the rods 60 were formed of a material with lower rigidity than the surrounding thin wall portion 64, the folding point could occur at the rod 60, as shown in FIG. 16. If the rods 60 were formed of a material with higher rigidity than the surrounding thin wall portion 64, the folding point could occur in the thin wall portion 64, at a position between two adjacent rods. The predictable unfolding pattern translates to a consistent push force. The lowered push force and increased push force consistency that results from including longitudinal rods in the thin wall portion 64 can be especially beneficial for sheaths having small outer diameters, for example from about 10 French to about 14 French, including about 10 French, about 11 French, about 12 French, about 13 French, and about 14 French.

Figure 7A:
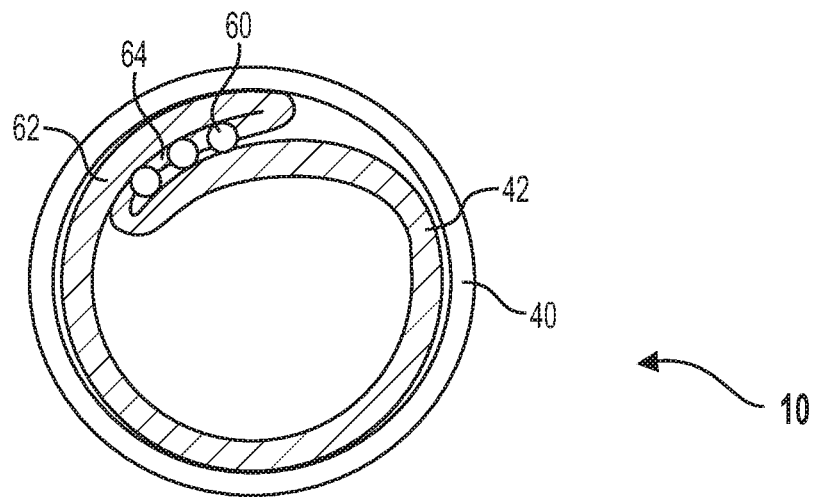
FIGS. 7A-7C are cross-sections of an example sheath including longitudinal rods in the inner tubular layer.
Figure 7B:
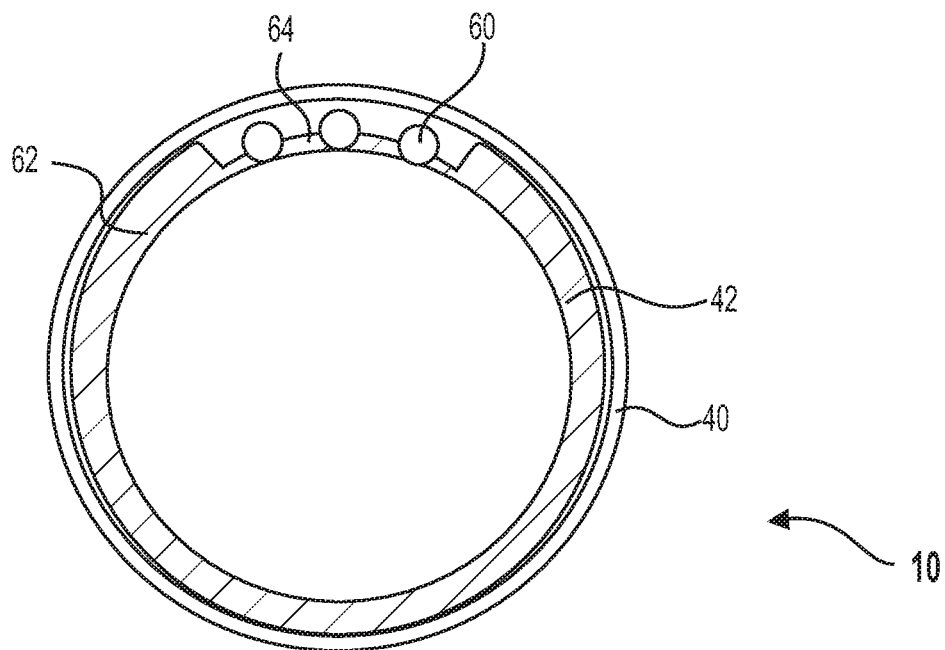
Figure 7C:
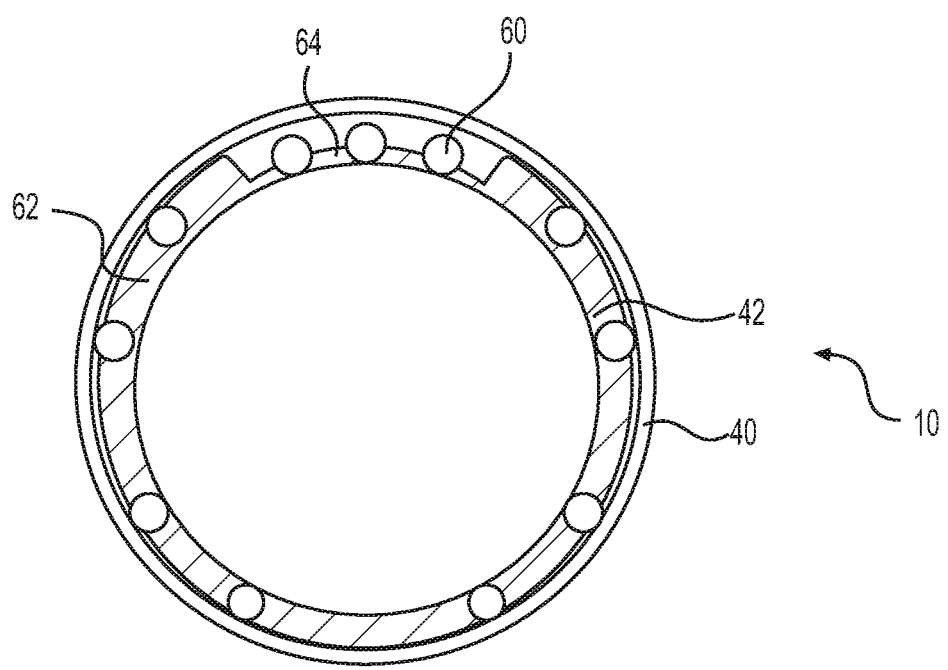

FIGS. 7A-7C provide another example of sheath 10 including a plurality of longitudinal rods 60 coupled to the inner tubular layer 42. Longitudinal rods 60 can be embedded within just the thin wall portion 64, as shown in FIGS. 7A and 7B, or the longitudinal rods 60 can be embedded within and spaced around both the thick wall portion 62 and the thin wall portion 64, as shown in FIG. 7C. The length or width of a longitudinal rod 60 positioned in the thin wall portion 64 of inner tubular layer 42 can be the same size as longitudinal rods 60 positioned in the thick wall portion 62, or a different size. The longitudinal rods 60 are positioned such that they protrude from the outer surface of the inner tubular layer 42, toward the outer tubular layer 40. In the non-expanded state shown in FIG. 7A, the longitudinal rods 60 of the thin wall portion 64 contact the thick wall portion 62 on the outer surface of the inner tubular layer 42.

Figure 8A:
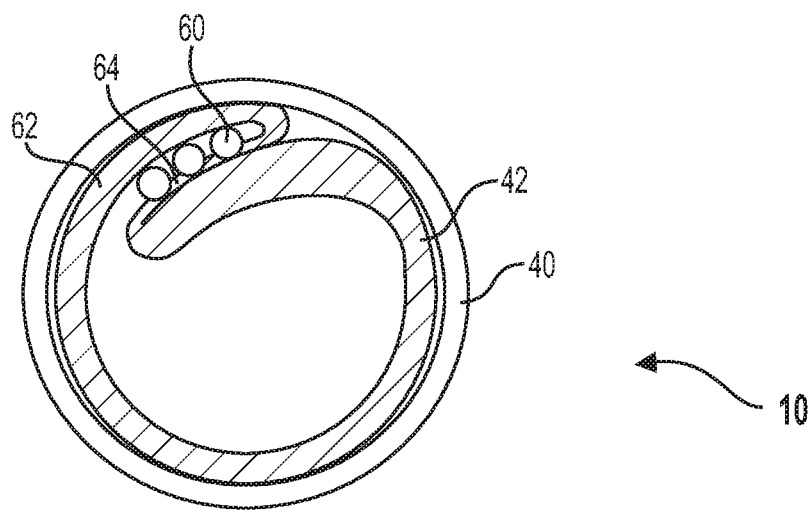
FIGS. 8A-8C are cross-sections of an example sheath including longitudinal rods in the inner tubular layer.
Figure 8B:
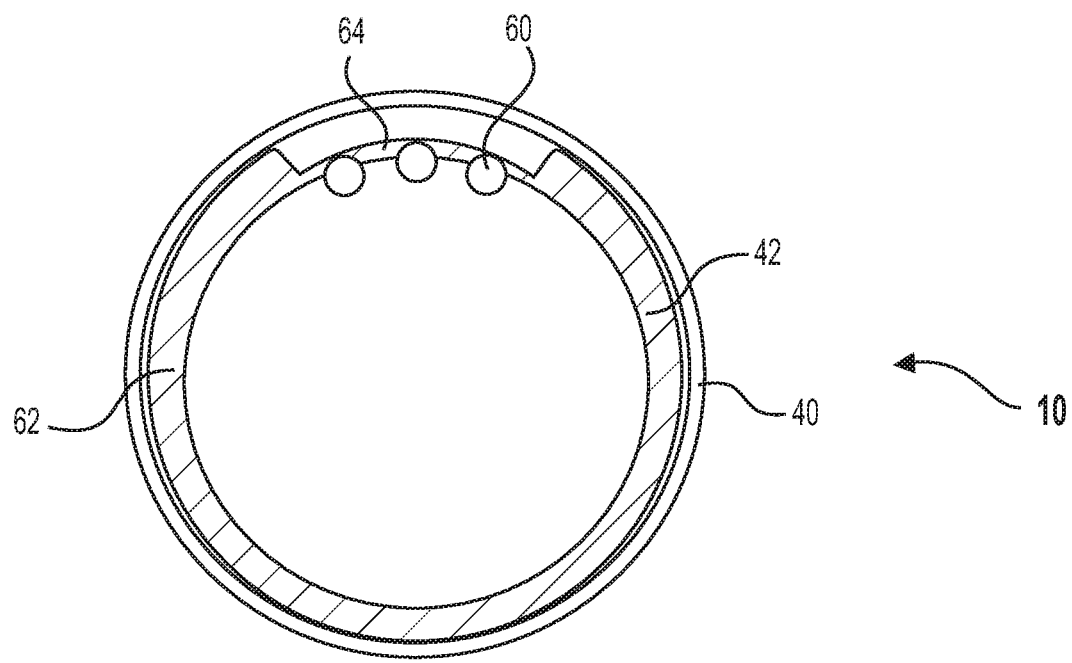
Figure 8C:
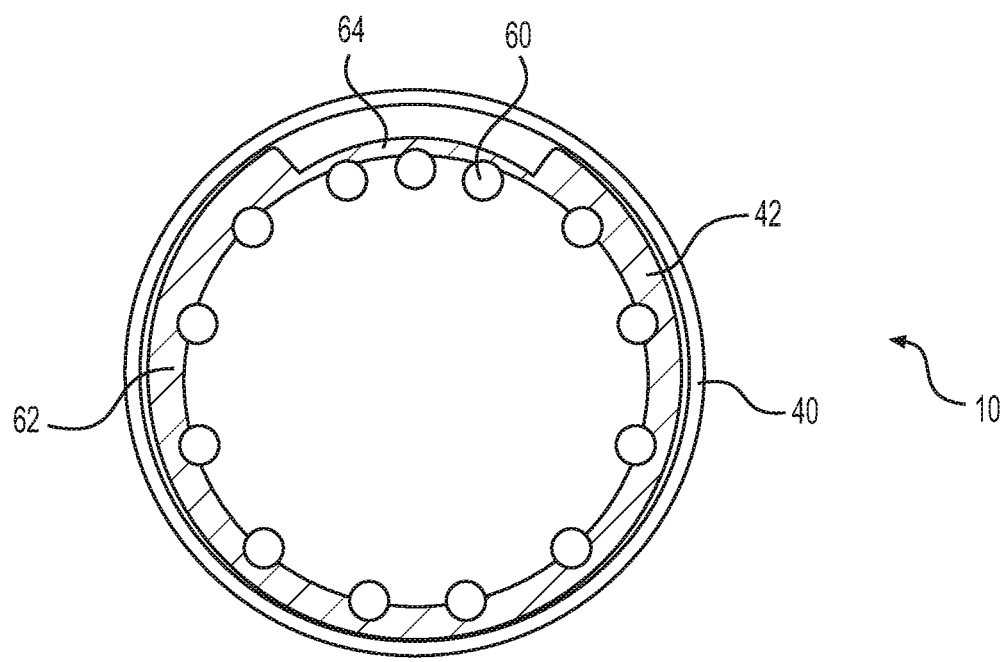

FIGS. 8A-8C provide another example sheath 10 including a plurality of longitudinal rods 60 coupled to the inner tubular layer 42. Longitudinal rods 60 can be embedded within just the thin wall portion 64, as shown in FIGS. 8A and 8B, or the longitudinal rods 60 can be embedded within and spaced around both the thick wall portion 62 and the thin wall portion 64, as shown in FIG. 8C. The length or width of a longitudinal rod 60 positioned in the thin wall portion 64 of inner tubular layer 42 can be the same size as longitudinal rods 60 positioned in the thick wall portion 62, or a different size. The longitudinal rods 60 are positioned such that they protrude from the inner surface of the thin wall portion 64 of inner tubular layer 42. In the non-expanded state, as illustrated in FIG. 8A, the longitudinal rods 60 come into contact with the thick wall portion 62 on the inner surface of inner tubular layer 42.

While the embodiments shown in FIGS. 6-8 illustrate three longitudinal rods 60 coupled to the thin wall portion 64, the number of longitudinal rods 60 can vary. Some embodiments can have as few as two or as many as 30 longitudinal rods 60 coupled to the thin wall portion 64. A large number of longitudinal rods 60—even 100 or more, depending upon their cross-sectional size, can be embedded in and spaced, evenly or unevenly, around the circumference of inner tubular layer 42. As described above, the cross-sectional shape of the longitudinal rods 60 can also vary. The longitudinal rods 60 shown in FIGS. 6-8 are circular in cross-section, but in other embodiments the longitudinal rods can be elliptical or semi-circular, or any other regular or irregular shape in cross-section. In some embodiments, the longitudinal rods 60 coupled to the inner tubular layer 42 extend the entire length of inner tubular layer 42. However, it is contemplated that in other embodiments, the longitudinal rods 60 will extend only a portion of the length of the inner tubular layer 42. In some embodiments, the inner tubular layer 42 can have longitudinal rods with a variety of radial positions. For example, some longitudinal rods 60 may protrude from both the inner and outer surfaces of the inner tubular layer 42, while other longitudinal rods 60 may protrude from just the inner surface, just the outer surface, or be entirely encapsulated within the inner tubular layer 42. It is further contemplated that longitudinal rods 60 can be included in only the thick wall portion 62 of the inner tubular layer 42. The longitudinal rods 60 can extend along the entire length of the inner tubular layer 42 or along a portion of the length of the inner tubular layer 42.

Figure 9:
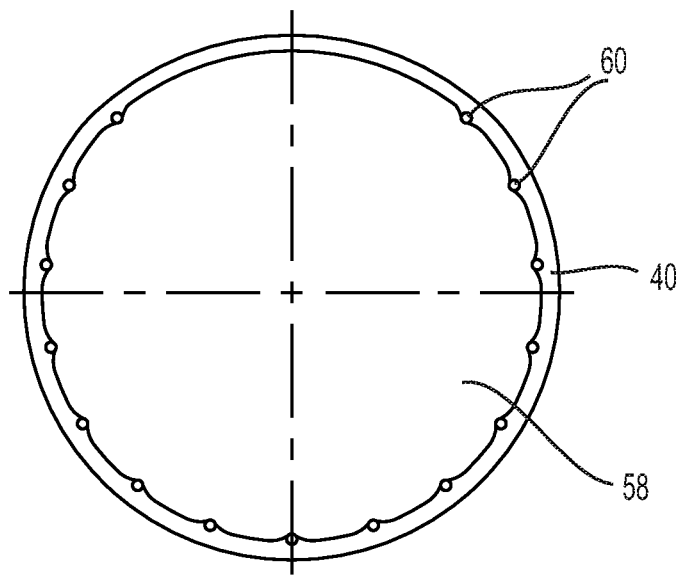
FIG. 9 is a cross-section of an example outer tubular layer of the sheath.

As shown in FIGS. 9-14, elastic outer tubular layer 40 can also include longitudinal rods 60. As illustrated in FIG. 9 the elastic outer tubular layer 40 can include a plurality of longitudinal rods 60. The longitudinal rods 60 extend the length of the outer tubular layer 40 and extend into the central lumen 58. The longitudinal rods 60 are coupled to the outer tubular layer 40, such as by being co-extruded and/or embedded into the elastic material of the outer tubular layer 40. Advantageously, the longitudinal rods 60 are configured to provide a bearing surface to facilitate relative movement of the inner tubular layer 42 within the outer tubular layer 40. This is especially helpful when the inner tubular layer 42 is unfolding and returning to its originally folded shape.

The longitudinal rods 60 can be circumferentially spaced about the inside surface of the outer tubular layer 60. Although fifteen longitudinal rods 60 are shown in the cross-section of FIG. 9, any number, including a single one, of longitudinal rods 60 can be employed. Also, the longitudinal rods 60 need not extend the entire length of the outer tubular layer 60. They can instead be applied selectively depending upon the demands of the implant, application and other circumstances. Longitudinal rods 60 can be selectively left out of an overall spacing pattern, such as in the embodiment shown in FIG. 9 where approximately 90-degrees of the inside surface of the outer tubular layer 40 is left as an unadorned surface.

Figure 10:
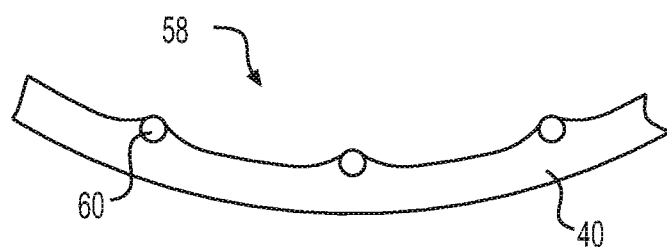
FIG. 10 is a magnified view of part of the outer tubular layer of FIG. 9, showing the cross section of longitudinal rods in greater detail.

FIG. 10 provides an enlarged view of a portion of the outer tubular layer 40 of FIG. 9. As shown in FIG. 10, the longitudinal rods 60 can have a circular cross-section so as to present a curved bearing surface into the lumen 58. In this manner, the longitudinal rods 60 space the inner tubular layer 42 from the inner surface of the outer tubular layer 40, thus reducing friction or the tendency to stick and impede relative movement. Although diameters for the longitudinal rods 60 can vary, in one embodiment they are 0.005+/−0.004 inches in diameter. In some examples, the longitudinal rods 60 extend from the inner surface of the outer tubular layer 40 about 0.004 inches. In other embodiments, the longitudinal rods 60 can define other shapes in cross-section. It is also contemplated that the cross-sectional shape of the longitudinal rod 60 can change along the sheath 10 in the longitudinal direction. As described above and illustrated in FIG. 10, the longitudinal rods 60 can be fully or partially encapsulated/enclosed within the material of the outer tubular layer 40. This prevents the longitudinal rods 60 from moving circumferentially and provides extra stability to the outer tubular layer 40. For example, as illustrated in FIG. 10, a majority of the perimeter of the longitudinal rods 60, i.e., more than 50-percent of the perimeter, can be enclosed within the outer tubular layer 40. As provided in FIG. 10, the wall thickness of the outer tubular layer 40 increases slightly proximate the longitudinal rod 60 such that the inner surface of the outer tubular layer 40 extends along the circumference of the longitudinal rod 60 to the portion where the rod 60 protrudes into the central lumen 58 of the outer tubular layer 40.

Figure 11:
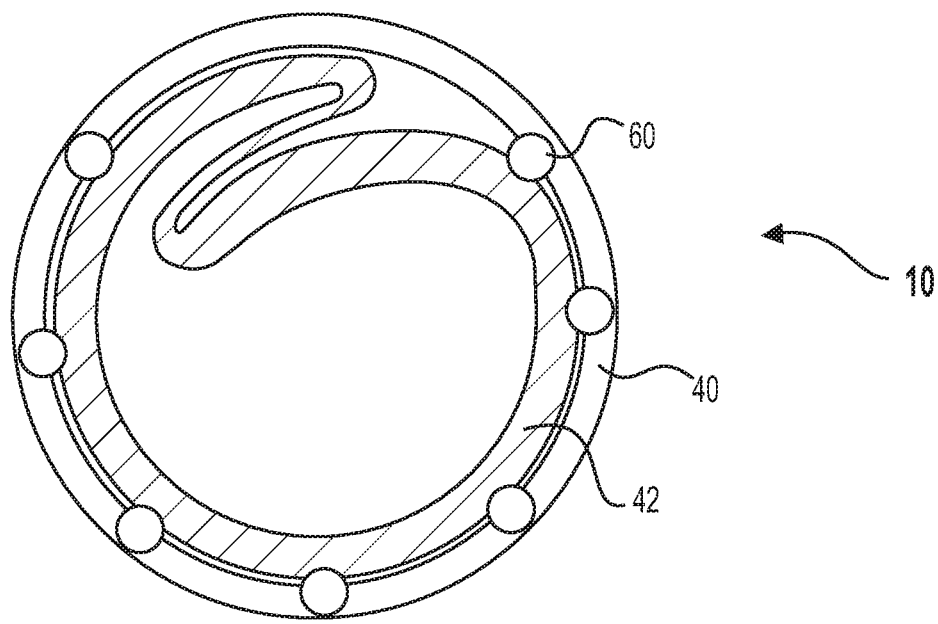
FIG. 11 is a cross-section of an example sheath including longitudinal rods embedded in the outer tubular layer.

FIG. 11 illustrates a sheath 10 including seven longitudinal rods 60 equally spaced from each other about the inner surface of the outer tubular layer 40 with the exception that a rod is missing from a portion adjacent the fold in the inner tubular layer 42. This gap in longitudinal rods 60 facilitates expansion and return of the inner tubular layer 42 to a non-expanded state. The gap in longitudinal rods 60 also functions as an anchor (a region of heightened friction) to prevent the outer tubular layer 40 from rotating against the inner tubular layer 42 during expansion and return of the sheath 10.

Figure 12:
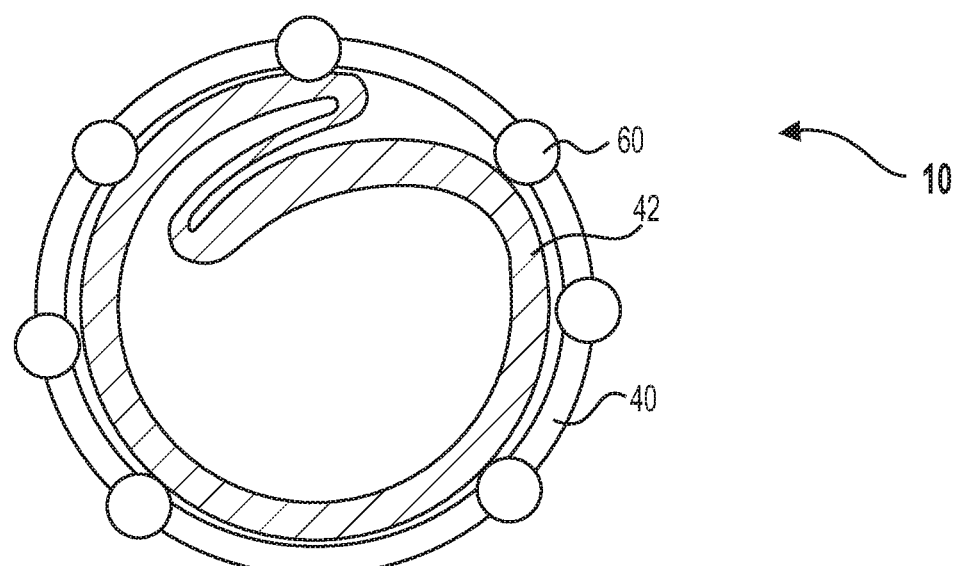
FIG. 12 is a cross-section of an example sheath including longitudinal rods embedded in the outer tubular layer.

FIG. 12 illustrates an example sheath 10 wherein longitudinal rods 60 are embedded in and spaced around the circumference of the outer tubular layer 40 with the exception that a rod 60 is missing from a portion opposite the fold in the inner tubular layer 42. This gap in the longitudinal rods 60 facilitates distraction and ensures that the portion of the outer tubular layer 40 without longitudinal rods 60 (the gap portion) functions as an anchor to prevent the outer tubular layer 40 from rotating against the inner tubular layer 42 during expansion and return of the sheath 10. As illustrated in FIG. 12, the longitudinal rods 60 protrude from the outer surface of the outer tubular layer 40 to lower friction between the sheath 10 and a body lumen or additional outer delivery sheath. The longitudinal rods 60 also protrude from the inner surface of the outer tubular layer 40 and into the central lumen 58 to lower friction between the outer tubular layer 40 and the inner tubular layer 42 during expansion and return of the inner tubular layer 42 to a non-expanded state.

Figure 13:
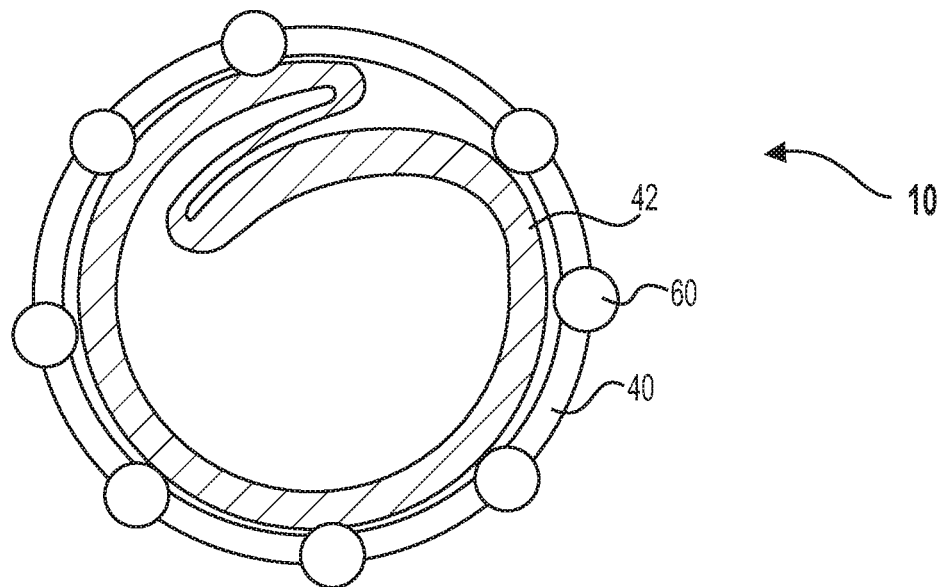
FIG. 13 is a cross-section of an example sheath including longitudinal rods embedded in the outer tubular layer.

FIG. 13 illustrates a similar rod arrangement to FIG. 11, but with eight longitudinal rods 60 embedded in and spaced around the circumference of outer tubular layer 40. Similar to the arrangement of FIG. 11, the rods 60 are offset from the location of the fold in the inner tubular layer 42 to facilitate expansion and return of the inner tubular layer 42 to a non-expanded state. Furthermore, the rods 60 of FIG. 13 protrude from the outer surface of the outer tubular layer 40 to lower friction between the sheath 10 and a body lumen or an additional outer delivery sheath. The longitudinal rods 60 also protrude from the inner surface of the outer tubular layer 40 and into the central lumen 58 to lower friction between the outer tubular layer 40 and the inner tubular layer 42 during expansion and return of the sheath 10 to a non-expanded state.

Figure 14:
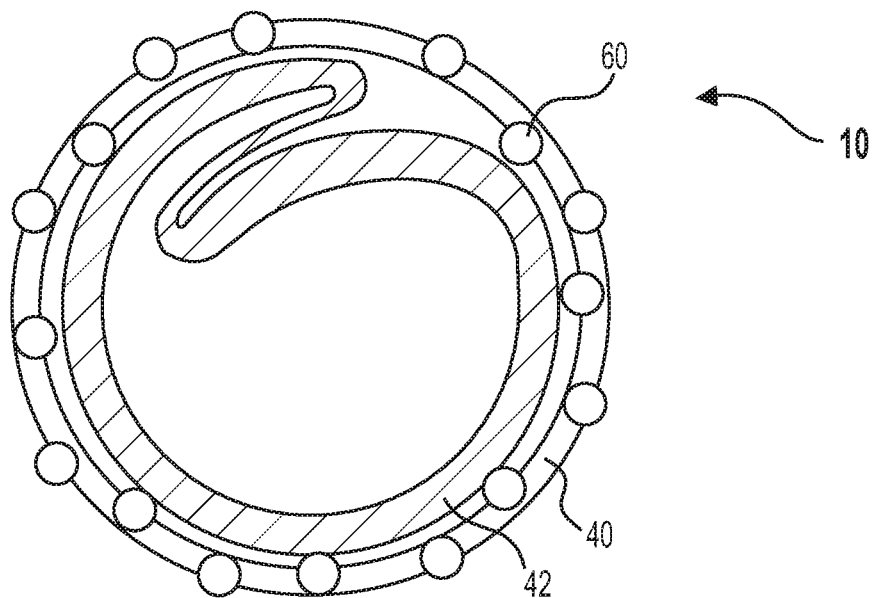
FIG. 14 is a cross-section of an example sheath including longitudinal rods embedded in the outer tubular layer.

FIG. 14 illustrates an example sheath 10 wherein longitudinal rods 60 are embedded in and spaced around the circumference of the outer tubular layer 40. As provided in FIG. 14, some of the longitudinal rods 60 protrude into the central lumen 58 of the outer tubular layer 42, and some of the longitudinal rods 60 protrude from the outer surface of the outer tubular layer 42. The inward and outward projection of the longitudinal rods 60 alternates around the circumference of the outer tubular layer 42. This can lower friction from advancement of the sheath 10 wherein, for example, the outer surface of the outer tubular layer 40 touches a body lumen or additional outer delivery sheath. The longitudinal rods 60 protruding from the inner surface of the outer tubular layer 40 and into the central lumen 58 lower friction between the outer tubular layer 40 and the inner tubular layer 42 during expansion and return of the sheath 10 to a non-expanded state.

Figure 15:
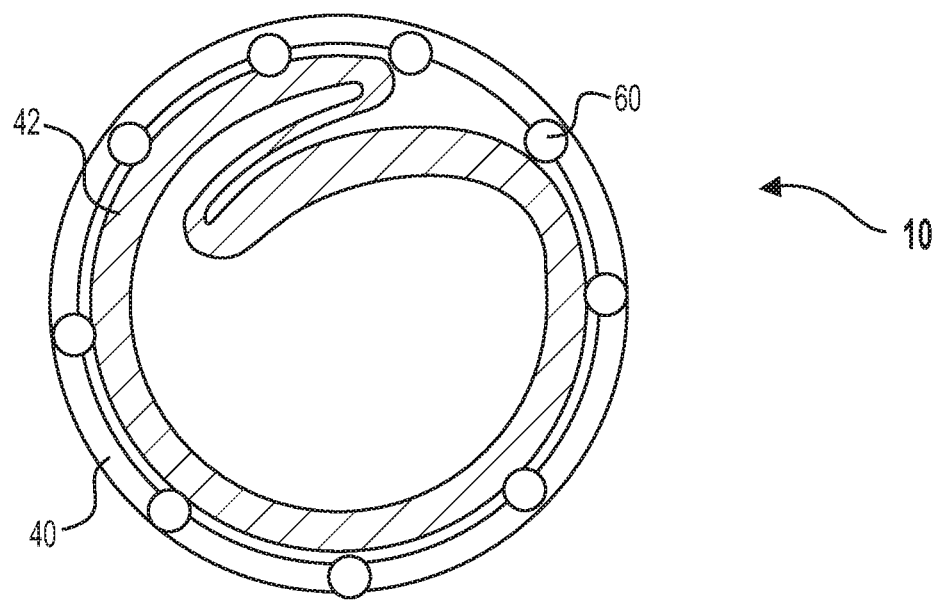
FIG. 15 is a cross-section of an example sheath including longitudinal rods embedded in the outer tubular layer and the inner tubular layer.

FIG. 15 provides another example sheath 10 wherein the longitudinal rods 60 are embedded in and spaced around the circumference of the outer tubular layer 40. The longitudinal rods 60 protrude from the inner surface of the outer tubular layer 40 and into the central lumen 58 to lower friction between the outer tubular layer 40 and the inner tubular layer 42 during expansion and return of the inner tubular layer 42 to a non-expanded state. As illustrated in FIG. 15, individual longitudinal rods 60 protrude into the central lumen 58 to various depths around the circumference of the outer tubular layer 40. Also, at least one of the longitudinal rods 60 protrudes from the outer surface of the outer tubular layer 40. It is also contemplated, and several longitudinal rods 60 can protrude from the outer surface of the outer tubular layer 40, and that the individual longitudinal rods 60 can protrude from the outer surface at varying distances.

In any of the embodiments, multiple longitudinal rods 60 may be spaced evenly or unevenly around the circumference of the inner tubular layer 42. Likewise, multiple longitudinal rods 60 can be spaced evenly or unevenly around the circumference of the outer tubular layer 40.

The outer tubular layer 40 in the configurations of FIGS. 9-15 can have a highly elastic and thin structure to fit over the inner tubular layer 42. The outer tubular layer 40 is not adhered to the inner tubular layer 42 allowing for free movement between the two layers. The outer tubular layer 40 is also seamless to guard against blood leakage. The outer tubular layer 40 promotes even stretching of sheath 10 in all radial directions—reducing the risk that the sheath 10 will tear during expansion. As described above, the elastic outer tubular layer 40 also urges the inner tubular layer 42 back into the non-expanded, reduced profile configuration. The outer tubular layer 40 can include a large number of longitudinal rods 60—even 100 or more depending upon their cross-sectional size. The longitudinal rods 60 can include microstructure patterns on their surfaces. For example, a microstructure pattern protruding from an outer surface of the longitudinal rod 60 can further reduce the contact surface between the longitudinal rod 60 and the inner tubular layer 42, further reducing friction between the two.

Expandable sheaths of the present disclosure can be used with various methods of introducing a prosthetic device into a patient's vasculature. Generally, during use, the expandable sheath 10 is passed through the skin of patient (usually over a guidewire) such that the distal end region of the expandable sheath 10 is inserted into a vessel, such as a femoral artery, and then advanced to a wider vessel, such as the abdominal aorta. The delivery apparatus 110 and its prosthetic device is then inserted through the expandable sheath 10 and advanced through the patient's vasculature until the prosthetic device is delivered to the implantation site and implanted within the patient. During the advance of the prosthetic device through the expandable sheath 10, the device and its delivery system exerts a radially outwardly directed force on a portion of the inner tubular layer 42, that portion of the inner tubular layer 42 exerts a corresponding radially outwardly directed force on a portion of the outer tubular layer 40, causing both the inner tubular layer 42 and the outer tubular layer 40 to expand locally to accommodate the profile of the device. The expansion of the inner tubular layer 42 causes the first and second longitudinally extending ends 66, 68 of the thick wall portion 62 to radially expand/separate. As a result, the thin wall portion 64 unfolds from its contracted state to define the expanded diameter of the inner tubular layer 42. As described above, during expansion, rods 60 provided on the inner tubular layer 42 and/or outer tubular layer 40 facilitate relative movement between the inner and outer layers 42, 40 and the passing device. The rods 60 provided on the thin wall portion 64 also facilitate an incremental or segmented expansion of the sheath 10. As outlined above, the inner tubular layer 42 will unfold progressively between the ends 66, 68 and the rods 60 (e.g., first incremental expansion provided between the first end 66 and the first adjacent rod 60, the second increment of expansion provided between the first rod 60 and the second rod 60, the third increment of expansion provided between the second rod 60 and the third rod 60, and the fourth increment of expansion provided between the third rod 60 and the end 68). It is contemplated that the incremental expansion may occur in any order between end 66 and end 68.

As the prosthetic device and its delivery system passes through the expandable sheath 10, the expandable sheath 10 recovers. That is, it returns to its original, non-expanded configuration. The outer tubular layer can provide an inwardly directed radial force to exert a compressive force urging the inner tubular layer 42 towards the non-expanded state. The outer tubular layer 40 can urge the first and second longitudinally extending ends 66, 68 toward and/or under, each other, after the passage of the prosthetic implant 112, such that the ends 66, and 68 of the inner tubular member 42 overlap when in the non-expanded state, with the thin wall portion 64 extending therebetween.

As described above, the expandable sheath 10 can be used to deliver, remove, repair, and/or replace a prosthetic device. In one example, the expandable sheath 10 described above can be used to deliver a prosthetic heart valve to a patient. For example, a heart valve (in a crimped or compressed state) can be placed on the distal end portion of an elongated delivery catheter and inserted into the sheath. Next, the delivery catheter and heart valve can be advanced through the patient's vasculature to the treatment site, where the valve is implanted.

Beyond transcatheter heart valves, the expandable sheath 10 can be useful for other types of minimally invasive surgery, such as any surgery requiring introduction of an apparatus into a subject's vessel. For example, the expandable sheath 10 can be used to introduce other types of delivery apparatus for placing various types of intraluminal devices (e.g., stents, stented grafts, balloon catheters for angioplasty procedures, etc.) into many types of vascular and non-vascular body lumens (e.g., veins, arteries, esophagus, ducts of the biliary tree, intestine, urethra, fallopian tube, other endocrine or exocrine ducts, etc.).

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above, but should be determined only by a fair reading of the claims that follow.

What is claimed is:

1. A method of delivering a prosthetic device into a patient, the method comprising:
    inserting an expandable sheath at an implantation site within a blood vessel of the patient, the sheath comprising an inner tubular layer having a thick wall portion and a thin wall portion extending between longitudinally extending ends of the thick wall portion, the thin wall portion comprising a first longitudinally extending reinforcing member extending along a length of the thin wall portion, the thick wall portion including a second longitudinally extending reinforcing member along a length of the thick wall portion;
    advancing the prosthetic device through a lumen of the sheath;
    locally expanding a portion of the sheath from a non-expanded state to an expanded state by a radially outward force exerted on an inner surface of the sheath by the advancement of the prosthetic device, such that expansion of the sheath causes the longitudinally extending ends of the thick wall portion to expand apart with the thin wall portion extending therebetween; and
    locally contracting the portion of the sheath from the expanded state at least partially back to the non-expanded state upon passage of the prosthetic device from the portion of the sheath;
    wherein the first longitudinally extending reinforcing member extends within the thin wall portion such that the first longitudinally extending reinforcing member has a thickness greater than a thickness of the thin wall portion, and
    wherein the second longitudinally extending reinforcing member extends within the thick wall portion such that the second longitudinally extending reinforcing member has a thickness less than a thickness of the thick wall portion.

2. The method of claim 1, wherein in the non-expanded state the longitudinally extending ends of the thick wall portion overlap such that the thin wall portion extends between an overlapping segment of the thick wall portion, wherein in the expanded state the longitudinally extending ends expand apart with the thin wall portion extending therebetween.

3. The method of claim 1, wherein the longitudinally extending ends of the thick wall portion include a first longitudinally extending end and a second longitudinally extending end, wherein locally expanding the portion of the sheath further comprises incrementally expanding the sheath, a first increment of expansion provided between the first longitudinally extending end and the first longitudinally extending reinforcing member, a second increment of expansion provided between the first longitudinally extending reinforcing member and the second longitudinally extending end.

4. The method of claim 1, wherein the longitudinally extending ends of the thick wall portion include a first longitudinally extending end and a second longitudinally extending end, wherein the thin wall portion of the sheath further includes a third longitudinally extending reinforcing member, the first longitudinally extending reinforcing member provided between the first longitudinally extending end and the third longitudinally extending reinforcing member, the third longitudinally extending reinforcing member provided between the first longitudinally extending reinforcing member and the second longitudinally extending end, wherein locally expanding the portion of the sheath further comprises incrementally expanding the sheath, a first increment of expansion provided between the first longitudinally extending end and the first reinforcing member, a second increment of expansion provided between first reinforcing member and the third reinforcing member, a third increment of expansion provided between the third reinforcing member and the second longitudinally extending end.

5. The method of claim 4, wherein the first and third longitudinally extending reinforcing members are formed of a material with a lower rigidity than an adjacent portion of the thin wall portion, wherein locally expanding the portion of the sheath causes a folding point of the thin wall portion to occur at one of the first and third longitudinally extending reinforcing members.

6. The method of claim 4, wherein the first and third longitudinally extending reinforcing members are formed of a material with a higher rigidity than an adjacent portion of the thin wall portion, wherein locally expanding the portion of the sheath causes a folding point of the thin wall portion to occur in the thin wall portion.

7. The method of claim 1, wherein locally contracting the sheath further comprises providing inwardly directed radial force of an elastic outer layer that exerts a radially compressive force urging the sheath towards the non-expanded state.

8. The method of claim 1, wherein the longitudinally extending ends of the thick wall portion include a first longitudinally extending end and a second longitudinally extending end,
wherein locally contracting the sheath further comprises moving the first and second longitudinally extending ends towards each other and into an overlapping configuration.

9. The method of claim 8, wherein moving the first and second longitudinally extending ends towards each other and into the overlapping configuration comprises moving the second end such that the thin wall portion extends between overlapping segments of the thick wall portion and is positioned radially between the overlapping segments of the thick wall portion.

10. The method of claim 9, wherein moving the first and second longitudinally extending ends towards each other and into the overlapping configuration comprises bringing the first longitudinally extending reinforcing member into contact with an inner surface of the thick wall portion.

11. The method of claim 1, wherein the first longitudinally extending reinforcing member protrudes from a surface of the thin wall portion of the inner tubular layer such that a protruding surface of the first longitudinally extending reinforcing member provides a bearing surface between the first longitudinally extending reinforcing member and the thick wall portion,
wherein locally expanding the portion of the sheath further comprises moving the protruding surface along the thick wall portion,
wherein locally contracting the portion of the sheath further comprises moving the protruding surface along the thick wall portion.

12. The method of claim 11, wherein a first protruding surface protrudes from an outer surface of the inner tubular layer and a second protruding surface protrudes from an inner surface of the inner tubular layer,
wherein, in the non-expanded state, the first protruding surface provides a bearing surface between the first longitudinally extending reinforcing member and an outer surface of the thick wall portion and the second protruding surface provide a bearing surface between the first longitudinally extending reinforcing member and an inner surface of the thick wall portion.

13. An expandable sheath comprising:
an inner tubular layer having a thick wall portion integrally connected to a thin wall portion, the thick wall portion having a first and second longitudinally extending end, the thin wall portion extending between the first and second longitudinally extending ends, the thin wall portion comprising a first longitudinal extending reinforcing member along a length of the thin wall portion, the thick wall portion including a second longitudinally extending reinforcing member along a length of the thick wall portion,
wherein the inner tubular layer is radially movable between an expanded state and a non-expanded state,
wherein in the non-expanded state the first longitudinally extending end is provided under the second longitudinally extending end of the inner tubular layer,
wherein in the expanded state the first and second longitudinally extending ends of the inner tubular layer expand apart with the thin wall portion extending therebetween,
wherein an outer surface of each of the first and second longitudinally extending reinforcing members protrude from a surface of the inner tubular layer,
wherein the first longitudinally extending reinforcing member extends within the thin wall portion such that the first longitudinally extending reinforcing member has a thickness greater than a thickness of the thin wall portion, and
wherein the second longitudinally extending reinforcing member extends within the thick wall portion such that the second longitudinally extending reinforcing member has a thickness less than a thickness of the thick wall portion.

14. The sheath of claim 13, wherein the outer surface of each of the first and second longitudinally extending reinforcing members protrude from an inner surface of the inner tubular layer such that a protruding surface of the first and second reinforcing members facilitate relative movement between the inner tubular layer and a passing device.

15. The sheath of claim 13, wherein the thin wall portion includes a plurality of first longitudinally extending reinforcing members spaced evenly circumferentially around the thin wall portion,
wherein the thick wall portion includes a plurality of second longitudinally extending reinforcing members spaced evenly circumferentially around the thin wall portion.

16. The sheath of claim 13, wherein the first longitudinally extending reinforcing member is formed of a material with a lower rigidity than an adjacent portion of the thin wall portion such that a folding point of the thin wall portion occurs at the first longitudinally extending reinforcing member when the sheath is moved between the expanded and non-expanded state.

17. The sheath of claim 13, wherein the first longitudinally extending reinforcing member is formed of a material with a higher rigidity than an adjacent portion of the thin wall portion such that a folding point of the thin wall portion to occur in the thin wall portion when the sheath is moved between the expanded and non-expanded state.

18. The sheath of claim 13, further comprising:
an elastic outer tubular layer radially movable with the inner tubular layer between the expanded state and non-expanded state,
wherein the elastic outer tubular layer urges the inner tubular layer towards the non-expanded state.

19. The sheath of claim 18, wherein a distal portion of the outer tubular layer and a distal portion of the inner tubular layer are adhered to each other in a sealed configuration.

* * * * *